United States Patent [19]

Barker

[11] 4,290,959
[45] Sep. 22, 1981

[54] PREPARATION OF PROPYLENE OXIDE
[75] Inventor: Robert S. Barker, Bloomfield, N.J.
[73] Assignee: Halcon Research and Development Corp., New York, N.Y.
[21] Appl. No.: 110,424
[22] Filed: Jan. 7, 1980

Related U.S. Application Data

[63] Continuation of Ser. No. 941,603, Sep. 11, 1978, abandoned, which is a continuation-in-part of Ser. No. 806,980, Jun. 16, 1977.

[51] Int. Cl.$^3$ ........................................... C07D 301/03
[52] U.S. Cl. ................................................. 260/348.24
[58] Field of Search ................................... 260/348.24

[56] References Cited

U.S. PATENT DOCUMENTS 3,452,047  6/1969  Frye ................................... 260/340.5
3,641,067  2/1972  Kruse ............................... 260/348.24
4,021,453  5/1977  Brill ................................. 260/348.24

FOREIGN PATENT DOCUMENTS 2255298  7/1975  France ............................ 260/348.24
13104    2/1974  Japan .

OTHER PUBLICATIONS

M. Kruse et al., J. Org. Chem., vol. 36, No. 8 (1971) pp. 1154–1155.

Primary Examiner—Norma S. Milestone
Attorney, Agent, or Firm—William C. Long; David Dick; Jack B. Murray, Jr.

[57] ABSTRACT

An improved process for preparing propylene oxide is provided in which propylene is oxidized by means of a thallic salt in the presence of aqueous media containing an alkanoic acid having at least seven carbon atoms and optionally in the presence of an organic solvent.

14 Claims, No Drawings

PREPARATION OF PROPYLENE OXIDE

REFERENCE TO RELATED APPLICATION

This is a continuation of application Ser. No. 941,603 filed Sept. 11, 1978, now abandoned, which was a continuation-in-part of application Ser. No. 806,980, filed June 16, 1977.

BACKGROUND OF THE INVENTION

1. Field of the Invention

This invention relates to the oxidation of propylene and is more particularly concerned with the preparation of propylene oxide by using thallic salts.

2. Statement of the Prior Art

Olefins have been oxidized with thallium triacetate in aqueous acetic acid to glycols and carbonyl compounds and in acetic acid and methanol to diacetate and ethers as well as allylic oxidation products. Exemplary of this art is U.S. Pat. No. 3,048,636 (issued in 1962 to R. R. Grinstead) in which a process is described for reaction of the olefin with at least an equimolar quantity of a thallium salt (chloride, nitrate, sulfate, or acetate) in acid solution in a solvent such as water, acetic acid, propionic acid, tetrahydrofuran, or methanol. But under these conditions the product of oxidation consists of a mixture formed solely of glycol and aldehyde or ketones. In the presence of a carboxylic acid, the carboxylic ester of the glycol will also be formed. The reaction, which may be carried out in favor of glycol class products as well as in the favor of the carbonylated products, will generally give rise to quite low yields of oxidation products.

U.S. Pat. No. 3,452,047 (issued in 1969 to A. H. Frye) also describes the oxidation of olefins by using a thallium salt, such as a nitrate or sulfate, in aqueous acid solution. This patent especially indicates that the utilization of a quantity of thallium salt lower by 10 to 90% than equimolecular quantity leads to preferential formation of aldehyde or ketone from the olefin.

W. Kruse et al., J. Org. Chem. 36 1154 (1971) describe the preparation of certain selected epoxides by the oxidation of the corresponding olefin with thallic acetate in weakly solvating media. Carbonyl by-products in the epoxidation of propylene in 50% (v/v) aqueous acetic acid were present in a propylene oxide to acetone molar ratio of 1:1, which ratio was improved to only about 4.5:1 by a use of a less polar solvent, tetrahydrofuran.

U.S. Pat. No. 3,641,067 (issued in 1972 to W. M. Kruse) also describes the preparation of the epoxide of propylene and isobutylene by means of lower alkyl thallic carboxylates, in the presence of a water-miscible organic solvent and an aliphatic monocarboxylic acid containing one to four carbon atoms, and describes use of pressures of up to 30 psi. Again propylene to acetone molar ratios in the products were found to be on the order of about 4.4:1.

Japanese Patent Publication No. 49-13104 (published in 1974) describes a process for converting $C_3$ to $C_5$ olefins to the corresponding epoxide wherein an aqueous aliphatic acid solution containing (1) a thallous salt, (2) an alkali or alkaline earth metal salt, and optionally a copper or iron salt of a fatty acid (acetic or propionic acid) or halide, and/or (3) an aliphatic carboxylic acid (acetic acid, propionic acid, etc.), is contacted with air or oxygen to oxidize the solution. The resulting oxidized solution is contacted with the olefin to form the desired epoxide by means of the thallic salt formed in the first step. Alternatively, the olefin may be present in the solution being oxidized so that a one-step process results.

This process is very difficult to control and the oxidation step is severely inefficient in conversion of a thallous salt to the thallic state required for subsequent oxidation of an olefin to the epoxide. Moreover, the lower aliphatic carboxylic acids employed did not cure the problems associated with previous processes as to the ratio of propylene oxide and by-product carbonyl compounds in the product mixture.

French Pat. No. 2,255,298 (issued in 1975 to Societe des Usines Chimiques Rhone-Poulenc) sought to improve the concentration of propylene epoxide in the product and to minimize the formation of acetone by a multi-step process of reacting propylene at a low temperature with an aqueous solution having a pH of not greater than 6 and containing a thallic salt of an aliphatic monocarboxylic acid having from one to four carbon atoms, a carboxylic acid which is miscible with or soluble in water, and a water-miscible organic solvent. (Aliphatic monocarboxylic acids of one to four carbon atoms are specified as being suitable.) The pH of the resulting reaction mixture is next critically adjusted to a value of at least 7 and the adjusted solution then heated, with immediate and rapid removal of the propylene oxide formed.

While French Pat. No. 2,255,298 achieves propylene oxide to acetone molar ratios of from about 10:1 to 16:1, the careful pH control required in this process is quite costly on an industrial scale.

U.S. Pat. No. 4,021,453 to William F. Brill discusses a process for preparing epoxides from the corresponding olefins by means of aryl thallic carboxylates having up to 12 carbon atoms in the presence of an inert polar organic solvent and in the presence of water, and optionally in the presence of free aryl carboxylic acid. The aryl thallic carboxylate is employed alone or in combination with a thallic alkanoate, with a ratio of aryl and non-aryl carboxylate being greater than 1:1, and can be formed in situ as by reacting the corresponding aryl carboxylic acid with thallic acetate.

SUMMARY OF THE INVENTION

In accordance with the process of the present invention, an improved process for preparing propylene oxide is provided wherein propylene is reacted with a thallic salt in the presence of water and an alkanoic acid having at least 7 carbon atoms and optionally in the presence of an organic solvent, to provide a product mixture containing propylene oxide and acetone having an improved propylene oxide to acetone molar ratio.

The discovery that the amount of acetone formed in the reaction of propylene to propylene oxide may be minimized by the use of the alkanoic acids of the present invention, is particularly surprising in view of the teachings of the prior art which have been limited to use of alkanoic acids having from 1 to 4 carbon atoms.

DETAILED DESCRIPTION OF THE INVENTION

The alkanoic acids employed in the practice of the process of the present invention are aliphatic monocarboxylic acids having at least 7 carbon atoms per molecule.

The alkanoic acids employed in the practice of this invention therefore include (a) monocarboxylic acids of the formula (I):

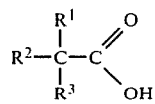

wherein $R^1$, $R^2$ and $R^3$ are the same or different and are selected from the group consisting of hydrogen, alkyl, aryl, cycloalkyl, alkaryl, aralkyl, and derivatives of the foregoing groups in which a non-carbonyl carbon is replaced by oxygen, and (b) halogenated derivatives of the above acids, with the proviso that the alkanoic acids contain a total of at least 7 carbon atoms, preferably at least 8 carbon atoms and more preferably at least 10 carbon atoms per molecule. While not critical to the present invention, the use of such alkanoic acids having in excess of 20 carbon atoms per molecule is generally not desired due to their relative expense in preparation. Preferably, when "$R^1$" is aryl or alkaryl, "$R^2$" and "$R^3$" are not both hydrogen.

Thus, the selected alkanoic acid can be straight-chain or (as is more preferred) branched-chain and can be unsubstituted or substituted. When "$R^1$", "$R^2$", or "$R^3$" is alkyl, the alkyl group can be branched- or straight-chained and is generally from 1 to 18 carbon atoms, preferably from 1 to 8 carbon atoms. Exemplary of such alkyl groups are methyl, ethyl, propyl, isopropyl, butyl, isobutyl, pentyl, hexyl, octyl, decyl, dodecyl, octadecyl and the like. When "$R^1$", "$R^2$", or "$R^3$" is aryl, the aryl group is generally phenyl, tolyl or naphthyl. When "$R^1$", "$R^2$", or "$R^3$" is cycloalkyl, the cycloalkyl group is generally from 3 to 12 carbon atoms, and preferably from 3 to 6 carbon atoms. Exemplary of such cycloalkyl groups are cyclopropyl, cyclohexyl, cyclodecyl, cyclododecyl, dicyclohexyl and the like. When "$R^1$", "$R^2$", or "$R^3$" is alkaryl, the aryl component generally consists of phenyl or tolyl and the alkyl component generally has from 1 to 12 carbon atoms, and preferably from 1 to 4 carbon atoms. Examples of such alkaryl groups are 3-tolyl, 4-ethyl phenyl, 3,5-xylyl, 4-isopropyl phenyl, 2-butyl, 4-pentyl phenyl and the like. When "$R^1$", "$R^2$", or "$R^3$" is aralkyl, the aryl group generally consists of phenyl or alkyl-substituted phenyl and the alkyl component generally has from 1 to 12 carbon atoms, and preferably from 1 to 4 carbon atoms. Examples of such aralkyl groups are benzyl, 7-(3'-ethyl phenyl) octyl, 2,2-diphenyl ethyl, and the like. Ether derivatives of the foregoing groups in which a non-carbonyl carbon is replaced by oxygen are, for example in the case of alkyl groups, exemplified by alkoxy-substituted alkyl such as 2-methoxy hexyl and 3-ethoxy propyl, and in the case of aralkyl groups, are inclusive of phenoxy-substituted alkyl such as phenoxy methyl, benzoxy ethyl, 4-phenoxyhexyl and the like.

Halogenated derivatives of the foregoing acids include acids in which one or more carbon-bonded hydrogens on one or more carbons are replaced by a halide (e.g., chloride, fluoride, bromide, or iodide).

Exemplary of alkanoic acids which may be employed, therefore, are straight-chained acids such as heptanoic acid, octanoic acid, decanoic acid, undecanoic acid, dodecanoic acid, tridecanoic acid, heptadecanoic acid, myristic acid, palmitic acid, stearic acid, and the like; branched-chain derivatives of the foregoing such as triethyl acetic acid, 3-methyl hexanoic acid, 2-methyl decanoic acid, 2-ethyl hexanoic acid, 4-ethyl nonanoic acid, and the like; and substituted and halogenated derivatives of the foregoing including cyclohexyl acetic acid, triphenyl acetic acid, 2-bromo-2-phenyl propionic acid, 2,3-diphenyl propionic acid, 2,2,3-triphenyl propionic acid, 2-ethyl-2-methyl butyric acid, 4-phenoxy butyric acid, and the like.

Exemplary of branched-chain alkanoic acids which can be employed are 2-ethyl hexanoic acid, 2-propyl hexanoic acid, 2-isobutyl-hexanoic acid and the like.

Preferred alkanoic acids in the above groups are those having a solubility in water at 20° C. of less than about 8 grams of acid per 100 grams of water, more preferably less than about 5 grams of acid per 100 grams of water, and most preferably less than about 4 grams of acid per 100 grams of water. Most preferably, the selected alkanoic acid is also water-immiscible, i.e., when mixed with water, spontaneously separates to form two separate liquid phases, one such liquid phase comprising the aqueous phase and the second comprising the alkanoic acid.

The selected acid should generally be used in an amount sufficient to provide from about 0.01 to 5 moles of acid per liter of liquid reaction medium, and preferably from about 0.05 to 1.0 mole of acid per liter of liquid reaction medium. Higher acid concentrations may be used, but are uneconomical.

The thallic salts which are suitably used in accordance with this invention include thallic salts of alkanoic acids containing 1 to 20 carbon atoms, and more preferably from 2 to 15 carbon atoms, which may be unsubstituted or substituted with non-reactive substituents such as halogen, alkoxy, alkyl and the like, thallic salts of aryl mono- and di-carboxylic acids containing up to 12 carbon atoms in the aryl moiety which can be unsubstituted or substituted with non-reactive substituents such as halogen, amino, alkoxy, alkyl and the like and mixtures of such thallic salts. Thus, examples of such thallic salts of alkanoic acids include thallic formate, thallic acetate, thallic propionate, thallic butyrate, thallic isobutyrate, thallic pentanoate, thallic hexanoate, thallic ethyl hexanoate, thallic heptanoate, thallic octanoate, thallic pivalate, thallic dodecanoate, thallic trifluoroacetate and the like, and examples of such thallic salts of aryl carboxylic acids include thallic benzoate, thallic toluate (i.e., salts of o-, m- and p-toluic acid), thallic nitrobenzoate, thallic phthalate, thallic chlorobenzoate, thallic dichlorobenzoate, thallic hydroxybenzoate, thallic ethylbenzoate, thallic anisate, thallic naphthanoate, thallic anthracate and the like. Of these groups of thallic salts, thallic alkanoates are preferred, and more preferred are thallic alkanoates having one to 12 carbon atoms, of which thallic 2-ethylhexanoate, thallic 2,2-dimethyl propionate, and thallic isobutyrate are especially preferred.

As indicated above, mixtures of different thallic salts can be employed. Preferably, however, only one thallic salt is used. It will, of course, be understood that the above thallic aryl carboxylic acid salts and thallic alkanoates can have other thallic salts mixed with them, but the alkanoates are preferably the sole thallic salts and preferably comprise more than 50 mole percent of total metallo-organic salts present. Most preferably, the thallic salt comprises a salt of the alkanoic acid selected for use.

Optionally, as is preferred, an organic solvent, which can be polar or non-polar (preferably polar), can be present in the reaction zone. Typical non-polar solvents include carbon tetrachloride and hydrocarbons such as ethane, butane and heptane. Typical polar organic solvents include cyclic ethers such as tetrahydrofuran and p-dioxane; alcohols such as t-butyl alcohol; amides such as dimethyl formamide and dimethyl acetamide; ketones such as acetone, methyl ethyl ketone and diethylketone; polar chlorinated hydrocarbons such as chloroform, as well as dimethyl sulfoxide, and the like; ethers of diethylene glycol and triethylene glycol; ether alcohols such as diethylene glycol, ethylene glycol monoethyl ether, ethylene glycol dimethyl ether, ethylene glycol diethyl ether, diethylene glycol monomethyl ether, diethylene glycol monoethyl ether, diethylene glycol mono-n-butyl ether and diethylene glycol diethyl ether; glycol esters such as ethylene glycol monoacetate, ethylene glycol diacetate, diethylene glycol monoacetate or diethylene glycol diacetate; and the corresponding ethers and esters of propylene glycol, butylene glycol and the like. It will be understood that the solvents mentioned above are merely representative of suitable solvents, and that the solvents may be miscible or immiscible with water.

The amount of water will generally fall between 0.1 and 50 volume percent of reaction medium but preferably from about 1 to 15 volume percent, and most preferably from about 2 to 7 volume percent. The amount of reaction medium is freely variable. Most suitably, however, enough is used to dissolve the thallic salt and to provide a molar ratio of water to thallic salt of at least 0.02:1, preferably at least 0.1:1. The selected alkanoic acid is suitably of at least about 5–15 volume percent of the total reaction medium. The thallic salt is typically employed in a concentration in the reaction medium of at least 0.05 M and preferably above 0.1 M.

The pH of the liquid reaction medium may vary widely but it is generally from about 1.5 to less than about 7, preferably from about 1.7 to 6.8, and more preferably from about 2 to 5.2. The foregoing pH values are those determined in the aqueous phase, where the liquid reaction medium comprises a two-phase liquid.

For further improved epoxide to acetone molar ratios, the reaction mixture preferably contains from about 1 to 10 mole percent, and preferably from about 5 to 10 mole percent, (based on the moles of thallic salt charged) of a buffer compound selected from the group consisting of salts of alkali metals and alkaline earth metals. Exemplary salts are the carbonates, bicarbonates, hydroxides, carboxylates, alkanoates, and the like whose solutions are alkaline. Preferred buffer compounds are the carboxylate salts of alkali metals and alkaline earth metals having from 1 to 20 carbon atoms, more preferably from 1 to 10 carbon atoms. Most preferred as buffer compound is the alkali metal or alkaline earth metal salt of the alkanoic acid selected for use in accordance with the process of the present invention. Suitable buffers therefore include sodium carbonate, potassium bicarbonate, rubidium hydroxide, sodium hydroxide, cesium acetate, strontium propionate, sodium octanoate, calcium pentanoate, magnesium heptanoate and barium decanoate.

The reaction can be carried out at any convenient temperature, e.g., 0° C., room temperature, or above, but for best results, from the standpoint of reaction rate, it is advantageous to heat the reaction mixture moderately, e.g., to temperatures of 25° to 180° C., preferably 30° to 120° C., but higher temperatures can be used as desired.

The reaction is suitably carried out in any vessel into which the alkanoic acid, water, solvent (if any) and the thallic salt can be charged and which will withstand pressure during reaction. The reaction vessel is provided with a suitable inlet tube for leading the propylene from its source into the liquid reaction mixture in the reaction or the reaction mixture can be pressured with propylene to the desired pressure before introduction into the vessel. The reaction can be carried out batch-wise or it can be run continuously. The propylene can be used in pure form or it can be diluted with an inert gas, e.g., nitrogen, argon, helium, or the like, if desired. The presence of a diluent will, of course, make it necessary to use a higher total pressure to provide the equivalent propylene pressure. Ordinarily, there is no advantage in employing total pressures greater than 300 psig, and there is no criticality of pressure used in the reaction zone in excess of that pressure necessary to maintain at least part of the alkanoic acid and water (and solvent, if any) in the liquid phase. It is generally advantageous to ensure good contact between the propylene, alkanoic acid and thallic salt in the liquid reaction mixture, and for this purpose efficient agitation, e.g., by mechanical means or by gas sparging of the propylene reactant or an inert gas (such as $N_2$), or otherwise, is suitably provided.

In the preferred embodiment of the improved process of the present invention, the propylene reactant is contacted with the selected thallic salt in the presence of water and an alkanoic acid of this invention at a temperature of from about 0° to 150° C., and most preferably from about 20° to 80° C., for a period of from about 10 minutes to 6 hours, and preferably from about 0.5 to 3 hours. At the end of the above period, the temperature of the reaction zone is increased from about 15° to 180° C., and preferably from about 30° to 120° C., for a further period of from about 1 to 240 minutes, and preferably from about 30 to 180 minutes. Most preferably, propylene oxide is rapidly eliminated from the reaction zone as it is formed, e.g., by sparging either propylene gas and/or an inert gas such as $N_2$ through the liquid reaction medium during the second, high-temperature step.

The product propylene oxide can also be readily recovered from the reaction mixture by distillation. Acetone will normally be formed as a minor by-product and can be separated from the propylene oxide in conventional manner, e.g., by distillation. Similarly, the thallium salts can also be recovered from the reaction mixture by distilling off the more volatile components. In the course of the reaction at least some of the thallic ion is reduced to the thallous state. If desired, the thallous ion can be reoxidized to the thallic state in any convenient manner to permit the formation of further quantities of thallic salt. In the event a gas sparging technique is used to provide agitation to the reaction mixture, or, as is preferred, to also rapidly eliminate the product propylene oxide from reaction zone as it is formed, the propylene oxide may be recovered from the gaseous effluent of the reaction zone by conventional condensation techniques and subsequent distillation of the condensate as described above.

The invention will be more fully understood by reference to the following specific examples, but it is to be understood that these examples are given solely for illustrative purposes and are not intended to be limitative of the invention. In the examples, the determination of propylene oxide and acetone is effected by gas chromatography employing a 10 ft.×⅛ in. Poropak-N filled column. In the examples that follow, and throughout this specification, parts are by weight unless otherwise indicated.

EXAMPLE 1

A mixture having a pH of about 2 and containing 9 parts of 2-ethyl hexanoic acid, 6 parts of water, 46 parts of ethylene glycol diacetate and 16 parts of tetrahydrofuran and having a 0.2 molar concentration of thallic triacetate is charged into a stirred pressure vessel. The vessel is pressured to 120 psig with propylene at 20° C., and is maintained at a temperature of 20° C. for 60 minutes. The vessel is then heated for 60 minutes at 70° C. with continuous stirring, after which the product mixture is found to have a pH of from about 4.2 to 5. The reaction mixture is then sparged with gaseous nitrogen. The gases are collected, condensed and analyzed using gas chromatography and are found to contain propylene oxide in a yield of about 80%, based on the thallic acetate charged. The molar ratio of propylene oxide to acetone in the product mixture is found to be about 32:1.

EXAMPLE 2

Example 1 is repeated except that the mixture charged to the pressure vessel also contains 5 mole percent of cesium acetate, based on the moles of thallic salt charged and has a pH of about 5. The product mixture is found to have a pH of from about 4.7 to 6. The condensed gases are found to contain propylene oxide in a yield of about 85%, based on the thallic acetate charged. The molar ratio of propylene oxide to acetone in the product mixture is found to be about 38:1.

EXAMPLE 3

A mixture having a pH of about 2 and containing 3.9 parts of thallic 2-ethylhexanoate, 5.5 parts of 2-ethylhexanoic acid, 1.0 part of water, and 28 parts of the diethyl ether of diethylene glycol is charged to a stirred pressure vessel. The vessel is pressured to 120 psig with propylene at 20° C., and is maintained at 20° C. for a period of one hour. The vessel is then heated to 70° C. for one hour with continuous stirring, allowing the pressure in the vessel to rise to about 250 psig. The vessel is cooled to 10° C., the propylene pressure is released and the product mixture (pH of about 4.2 to 5) is analyzed for propylene oxide. The product mixture is found to contain propylene oxide in a yield of about 66%, based on the thallic salt charged, and the molar ratio of propylene oxide to acetone in the product mixture is found to be about 40:1.

EXAMPLE 4

The thallic salt of 2-(n-butyl)-2-ethyl pentanoic acid (i.e., neodecanoic acid) is prepared by mixing 10 parts of thallic acetate with 37 parts of 2-(n-butyl)-2-ethyl pentanoic acid at 50° C. under continuous stirring for a period of one hour. After this period, the acetic acid freed by the reaction of the thallic acetate and the 2-(n-butyl)-2-ethyl pentanoic acid is removed under vacuum at 50° C., thereby resulting in 40 parts of liquid material containing 12 parts of 2-(n-butyl)-2-ethyl pentanoic acid and 28 parts of the desired thallic 2-(n-butyl)-2-ethyl pentanoate.

Following the procedure of Example 3, 10 parts of the mixture prepared above (i.e., 7 parts thallic 2(n-butyl)-2-ethyl pentanoate and 3 parts of 2-(n-butyl)-2-ethyl pentanoic acid), 2 parts water and 28 parts 1,2-dimethoxyethane are mixed and charged to a stirred pressure vessel. The mixture so charged to the stirred pressure vessel is found to have a pH of about 2. The vessel is pressured to 120 psig with propylene at 20° C., and is maintained at this temperature for a period of one hour. The vessel is then heated to 70° C. for 2 hours with continuous stirring, allowing the pressure in the vessel to rise to about 250 psig. The vessel is then cooled to a temperature of 10° C., the propylene pressure is released and the product mixture (pH of about 4.8 to 5) is analyzed for propylene oxide. The product mixture is found to contain propylene oxide in a yield of about 90%, based on the thallic salt charged. Only a trace of acetone is found, thereby giving a molar ratio of propylene oxide to acetone in the product mixture greater than 80:1.

EXAMPLE 5

A mixture having a pH of about 4 and containing 9 parts of heptanoic acid, 6 parts of water, 46 parts of ethylene glycol diacetate and 16 parts of tetrahydrofuran and 5.3 parts of thallic triacetate is charged into a stirred pressure vessel. The vessel is pressured to 120 psig with propylene at 20° C., and is maintained at a temperature of 20° C. for 60 minutes. The vessel is then heated for 3 hours at 60°–75° C. with continuous stirring, after which the vessel is cooled to 0° C., the propylene pressure is released and the product mixture (pH of about 5.6) is analyzed by gas chromatography. The molar ratio of propylene oxide to acetone in the product mixture is found to be about 14:1.

EXAMPLE 6 FOR COMPARISON

Example 5 is repeated except that the mixture charged to the pressure vessel contains 6 parts of n-butyric acid instead of heptanoic acid. The charged mixture and product mixture are found to have a pH of about 3.7 and about 5.9, respectively. The molar ratio of propylene oxide to acetone in the product mixture is found to be only about 8.9:1.

EXAMPLE 7 FOR COMPARISON

Example 5 is repeated except that the mixture charged to the pressure vessel contains 6 parts of acetic acid instead of heptanoic acid. The charged mixture and product mixture are found to have a pH of about 2 and from about 4.2 to 5, respectively. The propylene oxide to acetone molar ratio is found to be only about 5:1.

EXAMPLE 8 FOR COMPARISON

Example 1 is repeated except that the mixture charged to the pressure vessel contains 10 parts of isobutyric acid instead of 2-ethyl hexanoic acid. The charged mixture and product mixture are found to have a pH of about 2 and from about 4.2 to 5, respectively. The condensed gases are found to contain propylene oxide in a yield of only about 65%, and the molar ratio of propylene oxide to acetone is found to be only about 10:1.

EXAMPLE 9 FOR COMPARISON

Example 1 is repeated except that the mixture charged to the pressure vessel contains 10 parts of acetic acid instead of 2-ethyl hexanoic acid. The charged mixture and product mixture are found to have a pH of about 2 and from about 4.2 to 5, respectively. The condensed gases are found to contain propylene oxide in a yield of about 55%; with the propylene oxide to acetone molar ratio being found to be only about 5:1.

Thus, it is apparent that the process of the present invention allows propylene oxide to be produced in molar ratios of propylene oxide to acetone of up to 80:1 and more.

It will be obvious that various changes and modifications may be made without departing from the invention and it is intended, therefore, that all matter contained in the foregoing description shall be interpreted as illustrative only and not limitative of the invention.

What is claimed is:

1. A process for preparing propylene oxide which comprises contacting propylene in a reaction zone with a thallic salt consisting essentially of a thallic alkanoate derived from an alkanoic acid containing from 1 to 20 carbon atoms, in the presence of an acidic aqueous reaction medium consisting essentially of water, said thallic alkanoate and at least one alkanoic monocarboxylic acid which possesses at least seven carbon atoms per molecule and which is selected from the group consisting of (a) acids of the formula (I):

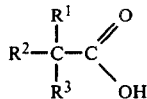

wherein $R^1$, $R^2$ and $R^3$ are the same or different and are selected from the group consisting of hydrogen, alkyl, aryl, cycloalkyl, alkaryl, aralkyl, and derivatives of the foregoing groups in which a non-carbonyl carbon is replaced by oxygen, and (b) halogenated derivatives of the above acids, with the proviso that when $R^1$ is aryl or alkaryl, $R^2$ and $R^3$ are not both hydrogen.

2. The process of claim 1 wherein said alkanoic monocarboxylic acid is water-immiscible.

3. The process of claim 1 wherein said alkanoic monocarboxylic acid possesses a solubility in water of less than about 8 grams of acid per 100 grams of water as determined at 25° C.

4. The process of claim 1 wherein the alkanoic monocarboxylic acid comprises at least one member of the group consisting of acids having a solubility in water at 20° C. of less than about 4 grams of acid per 100 grams of water.

5. The process of claim 1 wherein said alkanoic monocarboxylic acid is present in said reaction zone in an amount of at least 0.01 mole of acid per liter of liquid reaction medium.

6. The process of claim 1 wherein the propylene is contacted in the reaction zone at a temperature of from about 0° to 150° C. for a period of from about 10 minutes to 6 hours, and thereafter at a temperature of from about 15° to 180° C. for a further period of from about 1 to 240 minutes.

7. The improved process of 1 wherein the liquid reaction medium has a pH of from about 1.5 to less than about 7.

8. The process of claim 7 wherein the liquid reaction medium has a pH of from about 2 to 5.2.

9. The process of claim 1 wherein the reaction zone further contains from about 1 to 10 mole percent of a buffer compound selected from the group consisting of salts of alkali metals and alkaline earth metals.

10. The process of claim 1 wherein the alkanoic monocarboxylic acid comprises at least one member selected from the group consisting of (a) acids of the formula (I):

wherein $R^1$, $R^2$ and $R^3$ are the same or different and are selected from the group consisting of hydrogen, alkyl, aryl, cycloalkyl, alkaryl, aralkyl, and derivatives of the foregoing groups in which a non-carbonyl carbon is replaced by oxygen, and (b) halogenated derivatives of the above acids, with the proviso that when $R^1$ is aryl or alkaryl, $R^2$ and $R^3$ are not both hydrogen and with the further proviso that the alkanoic monocarboxylic acid is branch chained.

11. The process of claim 10 wherein said branched-chain alkanoic monocarboxylic acid contains from 7 to 20 carbon atoms per molecule.

12. The process of claim 11 wherein said alkanoic monocarboxylic acid has a solubility in water at 20° C. of less than about 4 grams of acid per 100 grams of water.

13. The process of claim 11 wherein said acid is water immiscible.

14. The process of claim 10 wherein said thallic salt consists essentially of a salt of said alkanoic monocarboxylic acid.

* * * * *